(12) United States Patent
Trabelsi et al.

(10) Patent No.: US 8,629,681 B1
(45) Date of Patent: Jan. 14, 2014

(54) MICROWAVE SENSOR AND ALGORITHM FOR MOISTURE AND DENSITY DETERMINATION

(75) Inventors: Samir Trabelsi, Athens, GA (US); Stuart O. Nelson, Athens, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 582 days.

(21) Appl. No.: 12/782,079

(22) Filed: May 18, 2010

Related U.S. Application Data

(60) Provisional application No. 61/179,212, filed on May 18, 2009.

(51) Int. Cl.
    *G01R 27/04* (2006.01)
(52) U.S. Cl.
    USPC ............... 324/639; 324/637; 324/640

(58) Field of Classification Search
    USPC ....................................... 324/640
    See application file for complete search history.

(56) References Cited

U.S. PATENT DOCUMENTS

| | | | | |
|---|---|---|---|---|
| 4,211,970 A | * | 7/1980 | Fitzky et al. | 324/634 |
| 4,270,083 A | * | 5/1981 | Fitzky et al. | 324/636 |
| 4,485,284 A | * | 11/1984 | Pakulis | 219/705 |
| 6,147,503 A | * | 11/2000 | Nelson et al. | 324/637 |
| 6,522,285 B2 | * | 2/2003 | Stolarczyk et al. | 342/22 |
| 6,566,637 B1 | * | 5/2003 | Revesz et al. | 219/679 |
| 6,691,563 B1 | * | 2/2004 | Trabelsi et al. | 73/73 |

* cited by examiner

*Primary Examiner* — Thomas F Valone
(74) *Attorney, Agent, or Firm* — Gail E. Poulos; Lesley M. Shaw; John D. Fado

(57) ABSTRACT

A microwave sensor and algorithm for instantaneous and nondestructive determination of bulk density and moisture content in granular or particulate materials at a single microwave frequency, especially agricultural commodities, which uses an inexpensive microwave circuit for determining the real and imaginary parts of relative complex permittivity using an algorithm for phase correction.

3 Claims, 9 Drawing Sheets

MICROWAVE SENSOR AND ALGORITHM FOR MOISTURE AND DENSITY DETERMINATION

REFERENCE TO RELATED APPLICATIONS

This application claims the benefit of U.S. provisional application No. 61/179,212, filed May 18, 2009, which is herein incorporated by reference in its entirety.

FIELD OF THE INVENTION

This invention relates to a microwave sensor operating at a single frequency for instantaneous and nondestructive determination of bulk density and moisture content in any granular or particulate material, especially in peanuts, grain and other seed. A microwave circuit and a novel phase-correction algorithm for the computation of dielectric properties from measurement of the attenuation and phase shift of a microwave signal are also disclosed.

BACKGROUND OF THE INVENTION

Moisture content of materials is a key parameter in many research and industrial applications, including the food and agriculture-related industries. The most widely used standard techniques for moisture content determination are oven drying techniques. These techniques are based on drying samples under specific conditions, such as temperature and time, depending on the material. Besides being energy and time consuming, in some instances the representative character of the samples might be questionable compared to the whole volume or mass of material under consideration. Moreover, most industrial processes are highly automated and require real-time, on-line measurement of the moisture content.

Electromagnetic wave-interaction-based techniques meet this requirement and provide a tool for continuous measurement. In this way, by averaging, a better estimate of the moisture content can be achieved. Among these techniques, free-space microwave measurement techniques have the advantages of being nondestructive and contactless. Therefore, they are suitable for on-line, real-time monitoring and control. However, with particulate materials, bulk density fluctuations, as material moves on a conveyor belt or flows through a chute or pipe, can produce significant errors in moisture content determination. It is possible to reduce these fluctuations by mechanical means by keeping the layer thickness constant or by using a vibrator to maintain an average density. However, this still produces unpredictable errors in moisture content because of the density effect. In this instance, the density has to be determined by a separate method, such as gamma-ray attenuation or weighing. A separate density measurement is always an additional cost with more technical complications in the design and implementation of the measuring system.

A better alternative is to identify empirically or define theoretically density-independent functions exclusively dependent on moisture content. From an industrial perspective, the concept of density independence is a convenient solution for a cost-effective sensor that fulfills specific requirements. Therefore, the density-independent functions should be easy to manipulate for moisture content computation and tolerate instabilities produced by the measuring system and the immediate environment as well. Most of the transmission systems for moisture content determination are based on the principle of two-parameter measurement, namely the attenuation $\Delta A$ and phase shift $\Delta \Phi$ and use of the ratio:

$$\Delta A / \Delta \Phi$$

as a density-independent function (Kraszewski et al., J. Microwave Power, Volume 12 (3), 241-252, 1977). This ratio was identified, empirically and can be used only in a transmission configuration over a limited moisture content range (Menke et al., IEEE MTT-S International Microwave Symposium Digest, Volume 3, 1415-1418, 1996).

To generalize the concept of density independence, the function has to be expressed in terms of universal entities such as the dielectric properties. The dielectric properties of materials are intrinsic properties usually expressed as the relative complex permittivity:

$$\epsilon = \epsilon' - j\epsilon''$$

where $\epsilon'$ is the dielectric constant, which represents the ability of a material to store electric energy, and $\epsilon''$ is the loss factor, which represents the loss of electric-field energy in the material. Another parameter often used to describe the amount of loss is the loss tangent, tan $\delta$, defined as the ratio:

$$\epsilon'' / \epsilon'.$$

The dielectric constant and loss factor, as well as the loss tangent, of moist substances are generally dependent on frequency, temperature, density, and moisture content. The influence of these variables on the relative complex permittivity has been explored and reported for many materials (Nelson et al., J. Agric. Eng. Res., Volume 21, 181-192, 1976; Kent, J. Microwave Power, Volume 12 (4), 341-345, 1977; Meyer et al., IEEE Trans. Microwave Theory Techn., Volume MTT-29 (7), 732-739, 1981; Nelson, Cereal Chemistry, Volume 58 (6), 487-492, 1981; Nelson, J. Microwave Power, Volume 18 (2), 143-153, 1983; Kress-Rogers et al., J. Food Eng., Volume 6, 345-376, 1987; Kraszewski et al., J. Microwave Power and Electromagn. Energy, Volume 31 (3), 135-141, 1996; Trabelsi et al., Microwave Power and Electromagn. Energy, Volume 32 (3), 188-194, 1997; Trabelsi et al., Meas. Sci. and Technol. 14, 589-600, 2003).

Present state-of-the-art microwave moisture measurement systems attempt to eliminate density fluctuation effects by secondary measurements of density with gamma radiation gauges or other techniques, or by taking the ratio of attenuation and phase-shift in microwave measurements. These techniques limit the errors in moisture content determination attributable to fluctuations in bulk density, but seldom do they eliminate the density effects entirely. Also, secondary measurements of density complicate measurement systems and increase their consequent costs.

For grains, moisture is an important factor affecting price paid for grain. Therefore, moisture content must be determined whenever grain is traded. If moisture content is too high at the time of harvest, the grain kernels can be damaged in the mechanical harvesting process, leaving them more susceptible to infection by fungi. If they are stored at moisture contents too high for the prevailing environment, they can spoil because of the action of microorganisms, and the value is degraded or completely lost for human and animal consumption. Reference methods for determining moisture in grain generally require oven drying at specified temperatures following prescribed laboratory procedures (ASAE, 2000, ASAE S352.2, American Society of Agricultural Engineers, St. Joseph, Mich., pp. 563), or chemical titration methods, which are also laboratory procedures. Therefore, these methods are too slow and tedious for practical use in the grain trade. Electrical measurement methods have been developed that depend on correlations between the electrical properties of the grain and moisture content (Nelson, Transactions of the ASAE, volume 8 (1), 38-48, 1965; Nelson, Journal of Microwave Power, volume 121(1), 67-72, 1977). Electrical meters for grain moisture determination have evolved over the past century (Nelson, IEEE Transactions on Electrical Insulation, Volume 26(5), 845-869, 1991), and grain moisture meters in the United States today are predominantly those operating from 1 to 20 MHz that sense the dielectric properties (relative permittivity) of the grain samples. These instruments, although troubled with inconsistency at moisture contents above 20% to 25% moisture content, perform reasonably well, and calibrations are maintained by the manufacturers for many different grain and seed commodities. Moisture meters used in the trade require static samples, and corrections are made for variations in temperature and bulk density of grain samples. Needs have long been recognized for moisture sensing instruments for applications with moving grain, and efforts have been devoted to developing RF dielectric type moisture monitoring instruments. The need for moisture monitoring on combines as grain is harvested has spurred such development. Modern agriculture, involving precision farming, which generally implies yield mapping with the application of global positioning systems and grain mass flow monitoring, requires reliable moisture monitoring also, because yield data need to be based on a specific moisture content. Fluctuation in bulk density when grain is flowing causes errors in moisture readings unless some compensation is provided for bulk density changes. Thus, moisture monitoring system design must provide some means for minimizing bulk density variation.

Research on sensing moisture content in grain by microwave measurements has indicated two important advantages for microwave frequencies. The inconsistency of moisture measurements by instruments operating in the high-frequency range may be due, in part, to the influence of ionic conduction on the measured dielectric properties at high moisture levels. At microwave frequencies, the influence of ionic conduction is negligible, and better correlations between permittivity and moisture content can be expected. In addition, techniques for density-independent moisture sensing in granular materials have been reported for measurements at microwave frequencies (Kraszewski, Journal of Microwave Power, Volume 23(4), 236-246, 1988; Kraszewski, Journal of Agricultural Engineering Research, Volume 71, 227-237, 1998; Kraszewski and Kulinski, IEEE Transactions on Industrial Electronics and Control Instrumentation, Volume 23(4), 364-370, 1976; Kraszewski et al., Journal of Agricultural Engineering Research, Volume 72, 27-35, 1999; Trabelsi et al, Electronics Letters, Volume 33(10), 874-876, 1997; Trabelsi et al, IEEE Transactions on Instrumentation and Measurement, Volume 47(1), 127-132, 1998a; Trabelsi and Nelson, Measurement Science and Technology, Volume 12, 2192-2197, 2001b). While various methods have been developed for measurement of properties of different materials, there remains a need in the art for a method for simultaneous, independent real-time measurements of bulk density and moisture content of materials. The present invention provides a method which is different from prior art methods and solves some of the problems associated with the measurement of density and moisture content of bulk materials.

SUMMARY OF THE INVENTION

It is therefore an object of the present invention to provide a microwave sensor for instantaneous and nondestructive determination of bulk density and moisture content in a granular or particulate material measured at a single microwave frequency.

A still further object of the present invention is to provide a microwave circuit for use with a microwave sensor which operates at a single microwave frequency and utilizes a novel algorithm for instantaneous and nondestructive determination of bulk density and moisture content in a granular or particulate material.

A still further object of the present invention is to provide a microwave circuit utilizing a novel algorithm for correctly calculating real and imaginary parts of complex permittivity from measurements of attenuation and phase shift of a wave traversing a granular or particulate material.

A still further object of the present invention is to provide a microwave sensor for instantaneous and nondestructive determination of bulk density and moisture content in a granular or particulate material wherein said sensor includes a microwave source, an isolator, a power splitter, a transmitting antenna, a receiving antenna, a temperature measurement device, a mixer, an analog-to-digital converter, a data acquisition and computing unit, and a sensor display.

Another object of the present invention is to provide a means for determining the real part and the imaginary part of the relative complex permittivity from single-frequency measurement of the attenuation and phase shift of a microwave signal after it traverses a sample material.

A still further object of the present invention is to provide a novel algorithm for phase correction, based on a linear relationship between the attenuation per unit thickness and the dielectric constant to resolve phase ambiguity for samples with thickness greater than the wavelength in the material.

Further objects and advantages of the present invention will be apparent from the following detailed description.

DETAILED DESCRIPTION OF THE INVENTION

Figure 1:
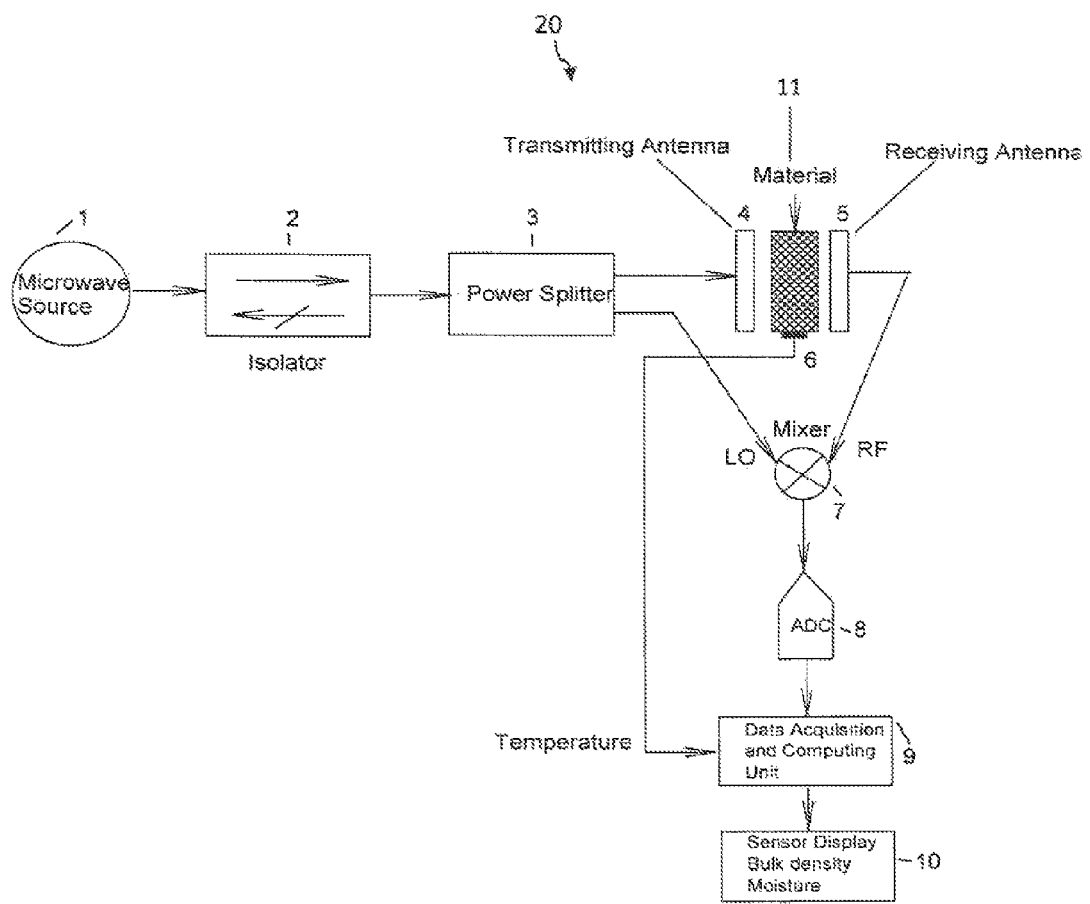
FIG. 1 is a drawing of a microwave sensor including a microwave source, an isolator, a power splitter, a transmitting antenna, a receiving antenna, a temperature measurement device, a mixer, an analog-to-digital converter, a data acquisition and computing unit, and a sensor display.

The present invention is a microwave sensor (FIG. 1), that includes a microwave circuit, operating at a single frequency for instantaneous and nondestructive determination of bulk density and moisture content of a granular or particulate material, such as for example, peanuts, grains, seeds, biofuel pellets, and other granular and particulate materials. The microwave circuit provides means for determining the real part and the imaginary part of the relative complex permittivity from measurement of the attenuation and phase shift of a microwave signal after it traverses the sample material under test. The circuit further includes a novel algorithm for phase correction (FIG. 9), based on a linear relationship between the attenuation per unit thickness and the dielectric constant and is used to resolve the phase ambiguity for samples with thickness greater than the wavelength in the material. The dielectric constant and dielectric loss factor are calculated from measurements of the attenuation and phase shift. Once the dielectric properties are determined, the bulk density of the material is calculated based on a complex-plane representation of the dielectric properties, and moisture content is determined with a density-independent calibration function expressed in terms of the dielectric properties. Also described is a method for moisture determination in a material using the microwave circuit of the present invention and measurements of dielectric properties.

Dielectric properties of materials are intrinsic electrical properties that characterize the interaction between the electric field of an electromagnetic wave and the material. They are represented by the relative complex permittivity $\in = \in' - j\in''$, where $\in'$ is the dielectric constant, $\in''$ is the dielectric loss factor, and $j=\sqrt{-1}$ is the imaginary unit. Both $\in'$ and $\in''$ are dependent on frequency, temperature, water content and composition of the material (Hasted, 1973, Nelson, 1981). At microwave frequencies, dielectric properties have been used for nondestructive simultaneous determination of moisture content and bulk density of granular and particulate materials (Trabelsi et al., 2000b. Method for the simultaneous and independent determination of moisture content and density of particulate materials from radio-frequency permittivity measurements, USA, U.S. Pat. No. 6,147,503; Trabelsi et al., 2004, Universal dielectric calibration method and apparatus for moisture content determination in particulate and granular materials, USA, U.S. Pat. No. 6,691,563). Accuracy and repeatability of moisture content and bulk density predictions rely mainly on the accuracy with which $\in'$ and $\in''$ are measured and the stability of the calibration equations correlating these properties with moisture content and bulk density. For accurate measurement of $\in'$ and $\in''$, sophisticated and expensive instruments such as impedance and vector network analyzers are often used. It is the object of this invention to provide an inexpensive microwave sensor operating at a single microwave frequency and associated algorithm for accurate determination of $\in'$ and $\in''$ that are used to determine moisture content and bulk density of the material.

Microwave Sensor

Many techniques can be used for measurement of the dielectric properties of a given material (Bussey, 1967. Measurement of the RF properties of materials, a survey. Proc. IEEE, 55(6), 1046-1053; Von Hippel, 1954. Dielectrics and Waves. John Wiley & Sons, New York). Among these, free-space techniques (reflection and transmission) have the advantages of being nondestructive, not requiring any sample preparation, and not requiring any physical contact with the material (Nyfors and Vainikainen, 1989. Industrial Microwave Systems. Artech House, Norwood, Mass., 351 pp.). The microwave sensor of the present invention is based on a free-space transmission technique in which $\in'$ and $\in''$ are determined from measurement of the attenuation and phase shift the incident wave undergoes when propagating through the material. FIG. 1 shows the diagram of the microwave sensor which is composed of the following elements:

1—Microwave source
2—Isolator
3—Power splitter
4—Transmitting antenna
5—Receiving antenna
6—Temperature measurement device
7—Mixer
8—Analog-to-digital converter
9—Data acquisition and computing unit
10—Sensor display
11—Sample The microwave source 1 is connected to an isolator 2 which will prevent any reflected signal from reaching the source 1. The isolator 2 is connected to a power splitter 3 with two output ports 1 and 2. The microwave signal at port 1 is the reference signal and is sent to the LO port of the mixer 7. The microwave signal at port 2 is sent to the transmitting antenna 4 which in turn radiates the electromagnetic energy into the material sample under test. Facing the transmitting antenna 4 is the receiving antenna 5 which collects the radiation after it traverses the sample 11 and sends it to the RF port of the mixer 7. In the mixer 7, the RF input is divided into two paths, in one path the RF input is mixed with the LO signal and provides the in-phase (I) signal, in the second path the RF signal is mixed with the 90-degree phase-shifted LO signal and provides the quadrature (Q) signal. Since both the LO and RF signals are at the same frequency, the voltages at the mixer outputs have dc values and are expressed as follows:

$$V_I = V_{RF} K \cos \theta \quad (1)$$

$$V_Q = V_{RF} K \sin \theta \quad (2)$$

$$\theta = \tan^{-1}\left(\frac{V_Q}{V_I}\right) \quad (3)$$

where $V_{RF}$ is the instantaneous peak RF voltage, K is the conversion loss of the mixer, and $\theta$ is the phase angle between the RF and LO signals. Both voltages $V_I$ and $V_Q$ and temperature T are fed to the data acquisition and computing unit 9 where $\in'$ and $\in''$ are calculated and moisture content and bulk density are determined. This will be explained in the following.

Frequency and Sample Dimensions Selection

The frequency is selected to avoid effects of ionic conduction which affect negatively the accuracy and repeatability of moisture content measurements (Trabelsi et al., 1998. New density-independent calibration function for microwave sensing of moisture content in particulate materials. IEEE Transactions on Instrumentation and Measurement, 47(3), 613-622). It is well established that the effect of ionic conduction is negligible at frequencies higher than 3 GHz (Hasted, 1973. Aqueous Dielectrics. Chapman and Hall, London). Also, to avoid electromagnetic wave scattering by the material, the wavelength of the incident wave should be larger than the size of granules or particles constituting the material.

Accuracy of attenuation measurements is affected by diffraction at the edges of the sample 11, multiple reflections, and scattering by the granules or particles. Diffraction at the edges of the sample can be minimized by selecting the transverse dimensions of the sample about three times the E-plane 3 dB beamwidth of the antenna (Chen et al., 2004. Microwave electronics. Wiley, West Sussex, England, 537 pp). Multiple reflections occur inside the sample, between the sample interfaces and the antennas and between the antennas through the sample. Effect of multiple reflections can be minimized by selecting a sample thickness (d) that ensures a minimum of 8 to 10 dB one-way attenuation and selecting the best matching condition between the two antennas 4 and 5. It was also observed that a minimum of a one-wavelength distance between each antenna 4 and 5 and the sample 11 is required. Finally, effects of scattering by the granules or particles can be reduced by proper selection of the frequency and material thickness (Trabelsi et al., 1999. Determining physical properties of grain by microwave permittivity measurements, Transactions of the ASAE, 42(2), 531-536; Trabelsi and Nelson, 2006. Nondestructive sensing of physical properties of granular materials by microwave permittivity measurement, IEEE Transactions on Instrumentation and Measurement, 55(3), 953-963).

Attenuation and Phase-Shift Determination

Attenuation and phase shift are determined by comparing the reference microwave signals measured without the sample to those obtained after the sample 11 is placed between the two antennas 4 and 5.

Attenuation is the difference between the power levels without the sample ($P_{RF,0}$) and with sample ($P_{RF,S}$) placed between the transmitting and receiving antennas 4 and 5. The power level at the RF port is calculated as:

$$P_{RF} = \frac{V_{RF}^2}{2R} \qquad (4)$$

where $V_{RF}$ is:

$$V_{RF} = \frac{V_I}{K\cos\theta} = \frac{V_Q}{K\sin\theta} \qquad (5)$$

And R is the input resistance to each device, which is 50Ω for a 50-Ω-based system.

The power level at the RF port can be expressed in dB as:

$$P_{RF}(dB) = 10\log\left[\frac{P_{RF}(W)}{1(W)}\right] \qquad (6)$$

The attenuation in dB is calculated from equations (4) through (6) as:

$$\Delta A(dB) = P_{RF,S}(dB) - P_{RF,0}(dB) \qquad (7)$$

Phase shift characterizes the delay in propagation caused by the slowing of speed of propagation of the wave in the medium. The phase shift is calculated as the difference between the phase measured without the sample 11 ($\theta_0$) and with sample 11 ($\theta_S$) placed between the transmitting and receiving antennas 4 and 5. The phase shift is calculated by using equations (1) through (3) as:

$$\Delta\theta(\text{rad}) = \theta_S - \theta_0 \qquad (8)$$

Because of the requirements cited above for accurate measurement of the attenuation, very often the sample 11 thickness is greater than the wavelength in the medium. Therefore, an ambiguity in phase determination occurs and there is need for a phase correction. Therefore, the actual phase shift is expressed as:

$$\Delta\theta_{actual}(\text{rad}) = (\theta_S - \theta_0) - 2\pi n \qquad (9)$$

where n is an integer to be determined. Solutions for resolving the phase ambiguity have been proposed (Musil and Zacek, 1986. Microwave Measurement of Complex Permittivity by Free Space Methods and Applications, Elsevier, New York, N.Y.; Trabelsi et al., 2000c. Phase-Shift ambiguity in microwave dielectric properties measurements, IEEE Transactions on Instrumentation and Measurement, 49(1), 56-60). However, they either require measurements at two frequencies or impose restrictions on the choice of the sample 11 thickness. A novel and original solution for the phase ambiguity problem will be described below.

Computation of the Dielectric Properties

The dielectric properties, real and imaginary parts, respectively, of the relative complex permittivity, $\varepsilon = \varepsilon' - j\varepsilon''$, are calculated from measurement of the attenuation and phase shift as follows:

$$\varepsilon' = \frac{\beta^2 - \alpha^2}{\beta_0^2} \qquad (10)$$

$$\varepsilon'' = \frac{2\alpha\beta}{\beta_0^2} \qquad (11)$$

where:

$$\alpha(Np/m) = \frac{\Delta A}{8.686 d} \qquad (12)$$

$$\beta(\text{rad}/m) = \beta_0 + \frac{\Delta\theta_{actual}}{d} \qquad (13)$$

$$\beta_0 = \frac{2\pi}{\lambda_0} \qquad (14)$$

$$\lambda_0 = \frac{c}{f} \qquad (15)$$

where $\lambda_0$ is the free-space wavelength, c is the speed of light in vacuum in m/s and f is the frequency in Hertz. Both $\Delta A$ and $\Delta\theta_{actual}$ are taken as positive numbers.

Algorithm for Phase Correction

Figure 2:
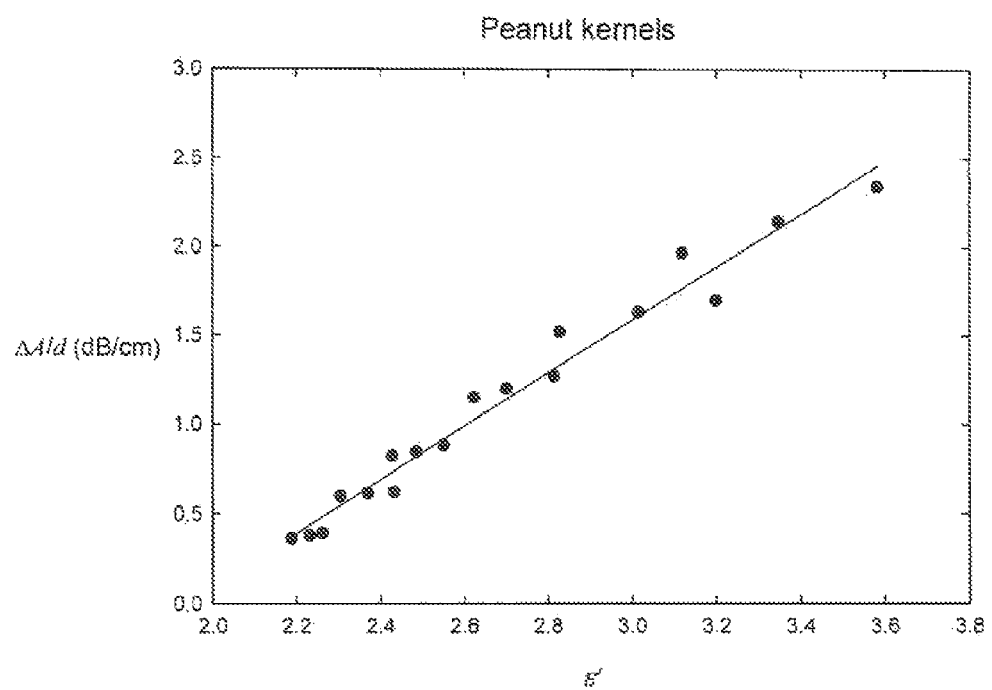
FIG. 2 is a graph showing the variation of attenuation divided by sample thickness as a function of dielectric constant of peanut kernels where f=approximately 5.8 GHz.
Figure 9:
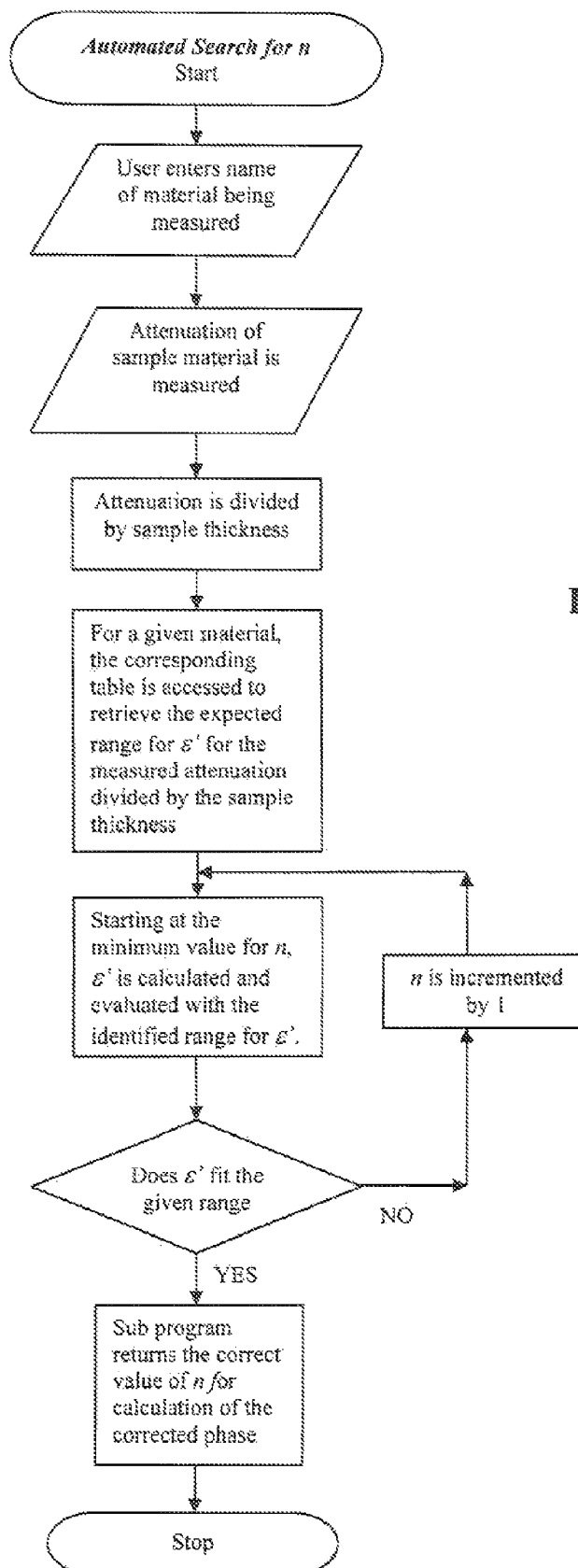
FIG. 9 is a flow diagram for the phase correction algorithm.

When the thickness of the sample 11 is greater than the wavelength in the sample 11, an ambiguity in the phase determination occurs and therefore the phase needs to be corrected for the computation of the dielectric properties of the sample 11. Available methods for phase correction require either measurements at two frequencies or measurements with two different thicknesses. There is no method for phase correction for measurements of dielectric properties at a single frequency and single sample 11 thickness. A novel phase correction algorithm of the present invention for phase correction for measurements of the dielectric properties at a single frequency without restrictions on the sample 11 thickness is disclosed (FIG. 9). The new phase correction algorithm uses the attenuation as an indicator to determine the expected range of $\varepsilon'$ and consequently the proper value of n to be used in equation 9. Once n is determined, the actual phase is calculated with equation 9 and the dielectric properties are computed from the attenuation (equation 7) and phase shift (equation 9) with equations 10 and 11 and subsequent set of equations 12-15. For this purpose, for a given sample 11, as a first step, the plot of attenuation divided by the material thickness ($\Delta A/d$) versus the dielectric constant ($\varepsilon'$) is obtained (FIG. 2). A table is generated from this plot, whereby for each range of attenuation divided by thickness a corresponding range for $\varepsilon'$ is identified. From this table, for each measured value of ΔA/d, the expected range for $\varepsilon'$ is determined. The phase ambiguity is resolved by looking for a value of n for which the calculated $\varepsilon'$ falls within that range. Note that none of the physical properties of the sample 11 including bulk density, moisture content, and temperature is needed in the phase correction algorithm.

Rather than starting the search for n (equation 9) with a random guess, the measured value of attenuation divided by the sample thickness is used to identify the range of expected dielectric constant s'. For purpose of illustration, refer to FIG. 2. Let's say the measured value of ΔA/d is between 0.5 and 1 dB/cm, then from FIG. 2, the expected range for $\varepsilon'$ is from 2.25 to 2.6. Starting with n=1 in equation (9), the dielectric constant $\varepsilon'$ is calculated with equation (10) and equations (12) through (15). If the value obtained for $\varepsilon'$ is within the range from 2.25 to 2.6, then n=1 is the solution. If the value obtained for $\varepsilon'$ is not within that range, then n is incremented by 1, and a new value of $\varepsilon'$ is calculated following the same procedure used for n=1. This process continues until a value of $\varepsilon'$ within the range from 2.25 to 2.6 is found. Once the phase ambiguity is resolved, $\varepsilon$'s is calculated with equation (11) and equations (12) through (15).

Simultaneous and Independent Determination of Bulk Density and Moisture Content

Once $\varepsilon'$ and $\varepsilon''$ are determined, a method covered in U.S. Pat. No. 6,147,503, issued Nov. 14, 2000 (Trabelsi et al., 2000b); herein incorporated by reference in its entirety, is used to determine moisture content and bulk density from measurement of the dielectric properties at a single microwave frequency.

Figure 3:
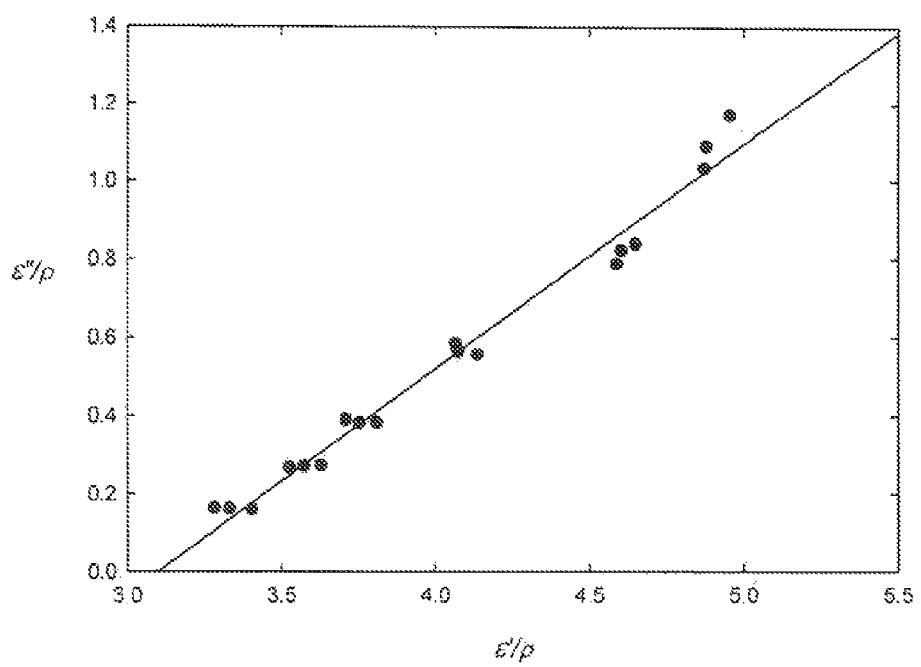
FIG. 3 is a graph showing the variation of dielectric loss factor divided by bulk density as a function of dielectric constant divided by bulk density for peanut kernels at f=approximately 5.8 GHz.

Bulk density is determined from a complex-plane representation of the dielectric properties $\varepsilon'$ and $\varepsilon''$ each divided by density as shown in FIG. 3.

To correlate dielectric loss factor divided by bulk density with dielectric constant divided by bulk density, a linear regression of the following form is used:

$$\frac{\varepsilon''}{\rho} = a_f\left(\frac{\varepsilon'}{\rho} - k\right) \quad (16)$$

For the results presented in FIG. 3, the slope $a_f$ was 0.577, the $\varepsilon'/\rho$-axis intercept k was 3.1, and the coefficient of determination $r^2$=0.98.

The bulk density is calculated from equation (16) without knowledge of the moisture content and temperature of the material as follows:

$$\rho = \frac{a_f\varepsilon' - \varepsilon''}{ka_f} \quad (17)$$

Figure 4:
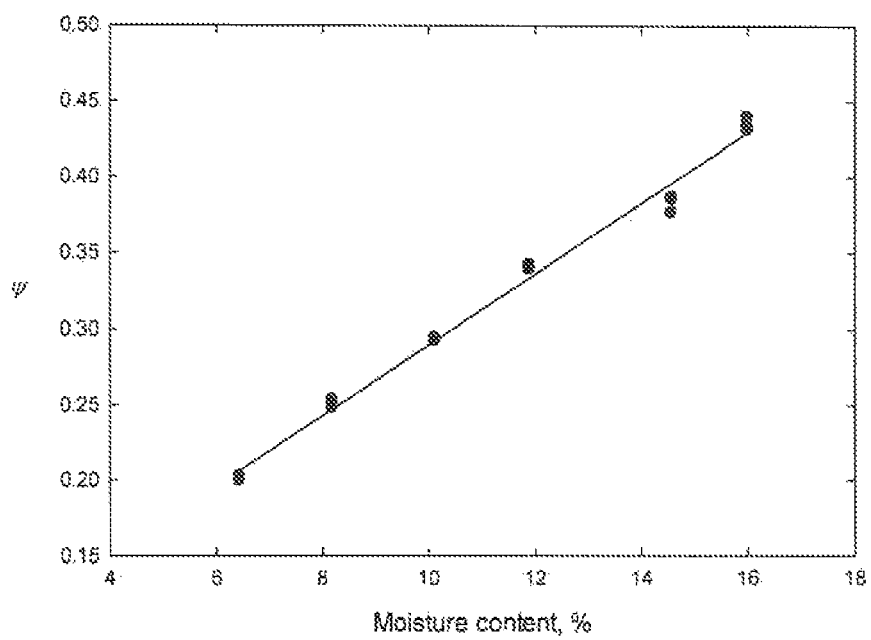
FIG. 4 is a graph showing the variation of a density-independent calibration function with moisture content at approximately 5.8 GHz and approximately 23 degrees C.

Moisture content is determined with a density-independent calibration function (Trabelsi et al., 2000a) expressed in terms of $\varepsilon'$ and $\varepsilon''$ as:

$$\psi = \sqrt{\frac{\varepsilon''}{\varepsilon'(a_f\varepsilon' - \varepsilon'')}} \quad (18)$$

where $a_f$ is the regression-line slope determined from complex-plane representation of the dielectric properties, each divided by bulk density, at a given frequency. For peanut kernels, $a_f$ was 0.577. The relationship between $\psi$ and moisture content is illustrated in FIG. 4.

A linear regression provides the relationship between $\psi$ and moisture content M:

$$\psi = 0.0233M + 0.056 \quad (19)$$

The coefficient of determination for equation (19) was 0.99. The moisture calibration equation can be obtained from equation (19):

$$M = \frac{\psi - 0.056}{0.023} \quad (20)$$

Apparatus

Figure 7:
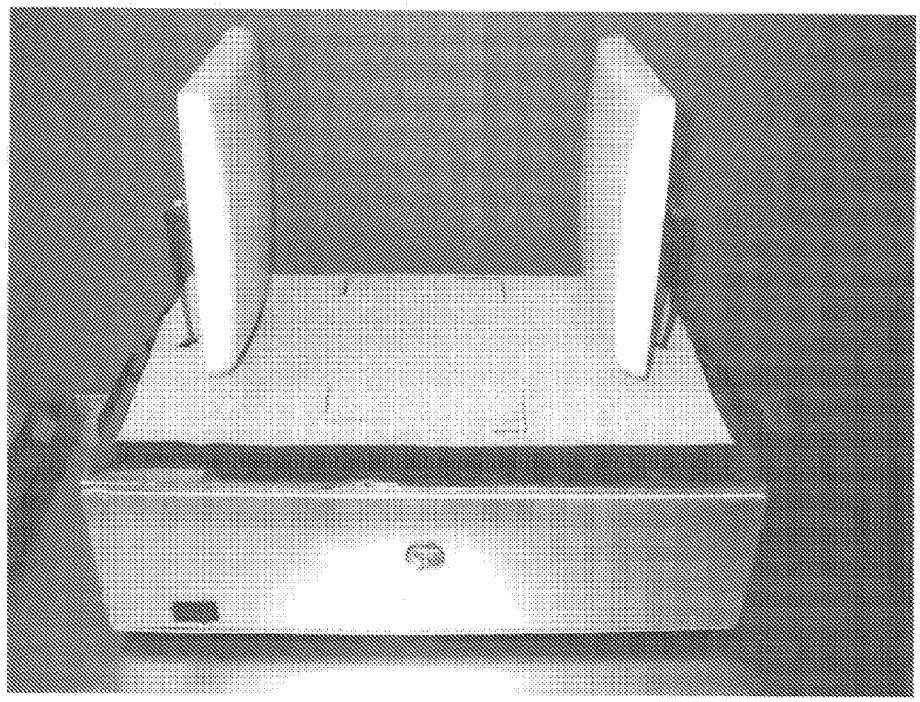
FIG. 7 is a photograph of the microwave sensor without an upper cabinet.
Figure 8:
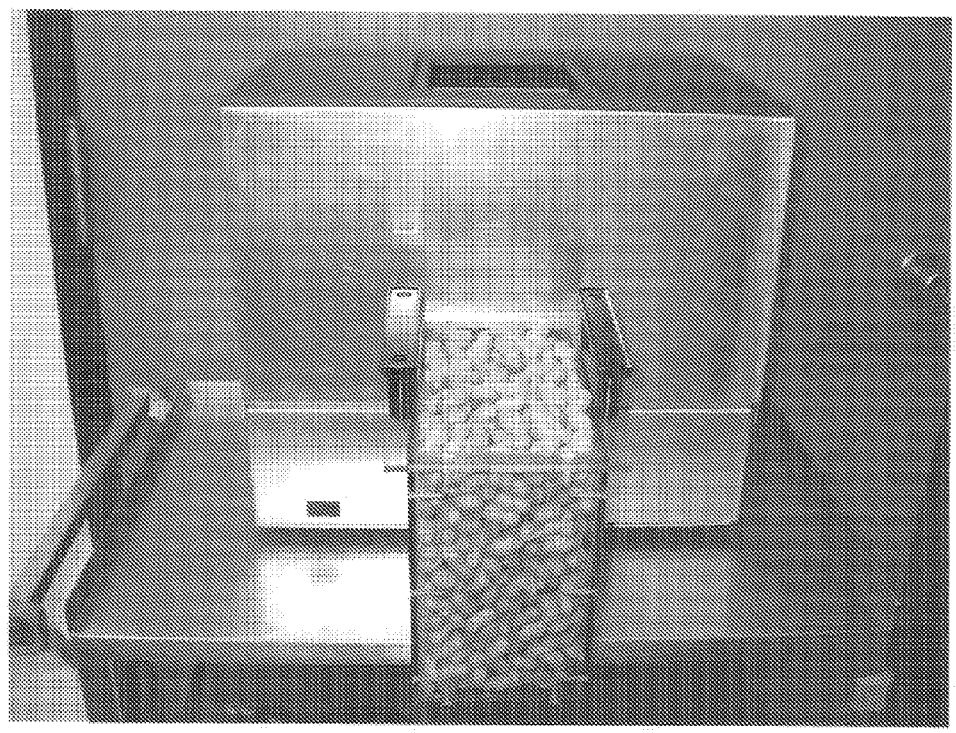
FIG. 8 is a photograph of the microwave sensor and sample holder bucket of the present invention wherein the sample holder bucket is filled with peanut pods.

The microwave sensor 20 of the present is housed in an aluminum cabinet of rectangular cross-section composed of two parts, a base cabinet and a cabinet cover. The base cabinet, which is a closed rectangular box about 18 inches wide, 12 inches deep, and 5 inches high, houses the microwave circuit components, fused power switch, power supply, cooling fan, and analog-to-digital interface, and serves as a mounting platform for the transmitting and receiving antennas, which face each other in alignment with L-shaped mounting brackets spaced 11½ inches apart above the base cabinet (FIG. 7). The cabinet cover consists of a four-sided rectangular aluminum box, 18 inches wide, 12 inches deep and 10 inches high with an open bottom, which rests on the base cabinet with end plates overlapping the base cabinet to facilitate mechanical attachment. The top of the cabinet cover consists of a ½-inch polyvinylchloride (PVC) plate with a 5¼ by 8¾ inch opening to accept a sample holding bucket, which is lowered into the chamber between the two antennas to place the sample in position between the antennas for the measurement (FIG. 8). When assembled to the cabinet base, the cabinet cover encloses the antennas and, with the top of the base cabinet, forms the antenna chamber for the microwave sensor. Sample holding buckets (FIG. 8) were fabricated from ¼-inch polycarbonate (Lexan) plate. They are a rectangular cross-section bucket with outside dimensions 5¼ inches wide, 8¾ inches deep and 8⅝ inches high with a ½-inch wide flange at the top that rests on a recessed lip of the opening in the PVC top of the cabinet to support and register the sample holding bucket in position between the two antennas. The Lexan buckets were assembled with cement and Nylon screws to avoid reflections of microwaves from metallic objects. The entire interior of the antenna chamber was lined with microwave absorbing material to prevent unwanted reflections that interfere with the desired measurements. Microwave circuit components were assembled and mounted on an aluminum plate suspended below the top of the base cabinet with aluminum posts. Coaxial cables connect the antennas through the top of the base cabinet to the microwave circuits housed in the base cabinet. A removable plate, forming the bottom of the base cabinet, was provided for assembly of the components and access for servicing the instrument. A filtered, circulating fan was mounted in one end of the base cabinet to provide cooling and ventilation for the components. The analog-to-digital converter was also mounted in the base cabinet with its cable connection socket available on the rear panel of the base cabinet for connection to a computer or microprocessor.

The following example is presented to illustrate the use of the present invention for moisture and density determination of a material sample. Peanuts are used as a test model in the present invention. The example is intended to illustrate the invention and is not intended to limit the scope of the defined claims.

Example 1

Figure 5:
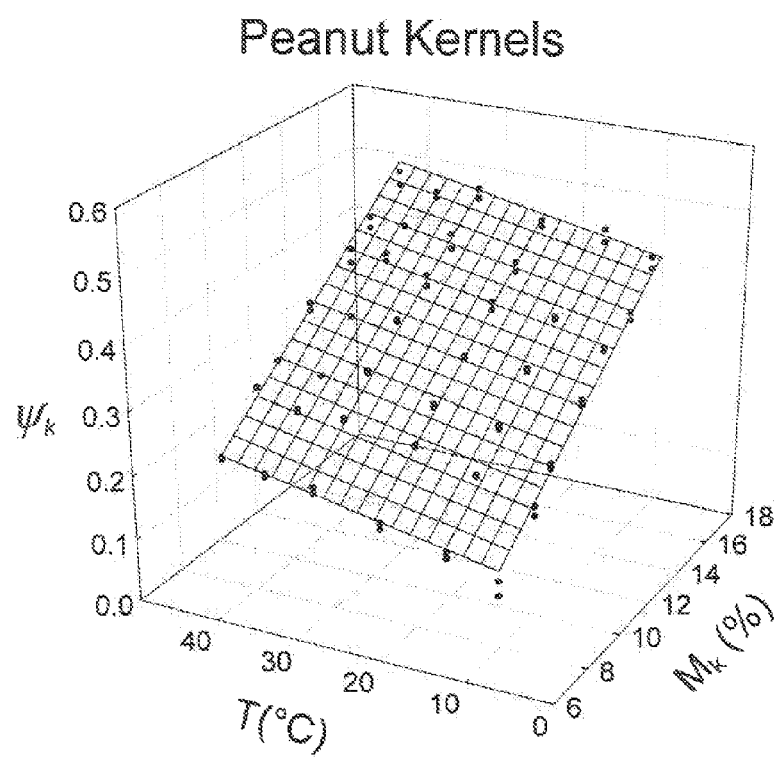
FIG. 5 is a graph showing the variation of a density-independent calibration function $\psi_k$ with moisture content $M_k$ and temperature T.
Figure 6:
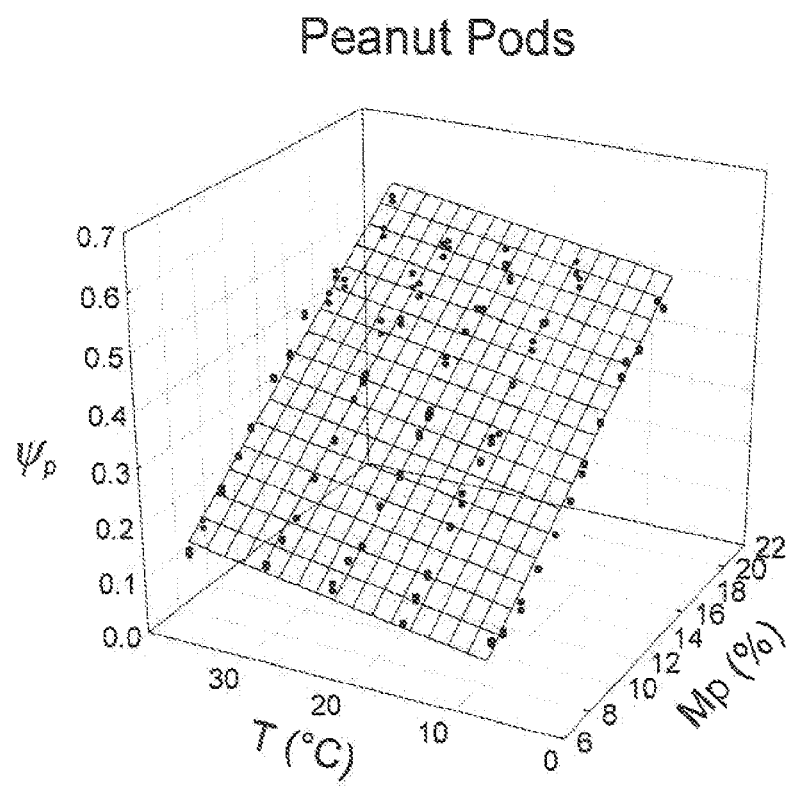
FIG. 6 is a graph showing the variation of a density-independent calibration function $\psi_p$ with moisture content $M_p$ and temperature T.

During the grading process, peanut pod samples are shelled and cleaned to determine the moisture content in the peanut kernels. This is somewhat tedious and time consuming. A method is disclosed for determining moisture content in peanut kernels from measurement of the dielectric properties of samples of clean or unclean peanut pods without having to shell them. The method only requires the introduction of pod samples to the sensor for an instantaneous determination of moisture content. Calibration of the sensor prior to use consists of collecting dielectric properties data for the peanut kernel and peanut pod samples of different moisture contents, bulk densities, and temperatures at a single microwave frequency. Then, the value of the density-independent calibration function given in equation (18) is calculated for each sample following the steps mentioned above. FIGS. 5 and 6 show the variations of $\psi_k$, for the kernels, and $\psi_p$, for the unshelled pods, with moisture content and temperature. For both materials, the data fall within a plane for which the equation can be obtained from a 3-D regression. The following equations were obtained:

For peanut kernels:

$$\psi_k = 0.028 M_k + 0.0025 T - 0.048 \, r^2 = 0.96 \quad (21)$$

For peanut pods:

$$\psi_p = 0.027 M_p + 0.003 T - 0.092 \, r^2 = 0.97 \quad (22)$$

By equating $\psi_k$ and $\psi_p$, a calibration equation for determining moisture content in peanut kernels from measurement on peanut pods is obtained:

$$M_k = \frac{\psi_p - 0.025 T + 0.048}{0.028} \quad (23)$$

Those skilled in the art will recognize that this invention may be embodied in other species than illustrated without departing from the spirit and scope of the essentials of this invention. The foregoing discussion is therefore to be considered illustrative and not restrictive. The scope of the invention is only limited by the appended claims.

REFERENCES

The following references are incorporated by reference in their entirety.

ASAE, 2000. ASAE 5352.2, American Society of Agricultural Engineers, St. Joseph, Mich., pp 563.
Bussey, H. E., 1967. Measurement of the RF properties of materials—A survey. Proc. IEEE, 55(6): 1046-1053.
Chen, L. F., Ong, C. K., Neo, C. P., Varadan, V. V. and Varadan, V. K., 2004. Microwave electronics. Wiley, West Sussex, England, 537 pp.
Hasted, J. B., 1973. Aqueous Dielectrics. Chapman and Hall, London.
Kent, J. 1977. Microwave Power, Volume 12 (4), 341-345.
Kraszewski and Kulinski, 1976. IEEE Transactions on Industrial Electronics and Control Instrumentation, Volume 23(4), 364-370.
Kraszewski et al., 1977. J. Microwave Power, Volume 12 (3), 241-252.
Kraszewski, 1988. Journal of Microwave Power, Volume 23(4), 236-246.
Kraszewski et al., 1996. J. Microwave Power and Electromagn. Energy, Volume 31 (3), 135-141.
Kraszewski, 1998. Journal of Agricultural Engineering Research, Volume 71, 227-237.
Kraszewski et al., 1999. Journal of Agricultural Engineering Research, Volume 72, 27-35.
Kress-Rogers et al., 1987. J. Food Eng., Volume 6, 345-376.
Menke et al., 1996. IEEE MTT-S International Microwave Symposium Digest, Volume 3, 1415-1418. Meyer et al., 1981. IEEE Trans. Microwave Theory Techn., Volume MTT-29 (7), 732-739.
Musil, J. and Zacek, F., 1986. Microwave Measurement of Complex Permittivity by Free Space Methods and Applications. Elsevier, New York, N.Y.
Nelson, 1965. Transactions of the ASAE, volume 8 (1), 38-48.
Nelson et al., 1976. J. Agric. Eng. Res., Volume 21, 181-192.
Nelson, 1977. Journal of Microwave Power, volume 121(1), 67-72. Nelson, 1981. Cereal Chemistry, Volume 58 (6), 487-492.
Nelson, J. 1983. Microwave Power, Volume 18 (2), 143-153.
Nelson, 1991. IEEE Transactions on Electrical Insulation, Volume 26(5), 845-869.
Nyfors, E. and Vainikainen, P., 1989. Industrial Microwave Sensors. Artech House, Norwood, Mass., 351 pp.
Trabelsi, S., Kraszewski, A. and Nelson, S., 2000a. Method for simultaneous and independent determination of moisture content and density of particulate materials from radio-frequency permittivity measurements, US Patent Office.
Trabelsi, S., Kraszewski, A. and Nelson, S., 2000b. Method for the simultaneous and independent determination of moisture content and density of particulate materials from radio-frequency permittivity measurements. U.S.A, U.S. Pat. No. 6,147,503.
Trabelsi, S., Kraszewski, A. and Nelson, S., 2004. Universal dielectric calibration method and apparatus for moisture content determination in particulate and granular materials, U.S. Pat. No. 6,691,563.
Trabelsi et al., 1997. Microwave Power and Electromagn. Energy, Volume 32 (3), 188-194.
Trabelsi et al, 1997. Electronics Letters, Volume 33(10), 874-876. Trabelsi, S., Kraszewski, A. and Nelson, S. O., 1998. New density-independent calibration function for microwave sensing of moisture content in particulate materials. IEEE Transactions on Instrumentation and Measurement, 47(3): 613-622.
Trabelsi et al, 1998a. IEEE Transactions on Instrumentation and Measurement, Volume 47(1), 127-132.
Trabelsi, S., Kraszewski, A. and Nelson, S. O., 1999. Determining physical properties of grain by microwave permittivity measurements. Transactions of the ASAE, 42(2): 531-536.
Trabelsi, S., Kraszewski, A. and Nelson, S. O., 2000c. Phase-shift ambiguity in microwave dielectric properties measurements. IEEE Transactions on Instrumentation and Measurement, 49(1): 56-60.
Trabelsi and Nelson, 2001b. Measurement Science and Technology, Volume 12, 2192-2197.
Trabelsi et al. 2003. Meas. Sci. and Technol. 14, 589-600.
Trabelsi, S. and Nelson, S., 2006. Nondestructive sensing of physical properties of granular materials by microwave permittivity measurement. IEEE Transactions on Instrumentation and Measurement, 55(3): 953-963.

Von Hippel, A. R., 1954. Dielectrics and Waves. John Wiley & Sons, New York.

INDEX OF THE ELEMENTS

1. Microwave Source
2. Isolator
3. Power Splitter
4. Transmitter
5. Receiver
6. Temperature. Measurement Device
7. Mixer
8. Analog to Digital Converter
9. Data Acquisition and Computing Unit.
10. Sensor Display
11. Sample
20. Microwave Sensor

We claim:

1. A system to measure bulk density and moisture content in a granular, powdered, or particulate matter comprising a microwave sensor operating at a single microwave frequency for instantaneous and nondestructive determination of bulk density and moisture content of a grain or particulate matter wherein said sensor includes a microwave circuit which provides a means for determining the real part and the imaginary part of the relative complex permittivity from attenuation and phase shift measurements when a microwave signal traverses said granular, powdered or particulate matter wherein said system includes a power splitter which splits said microwave signal prior to said granular, powdered or particulate matter and sends a reference signal from a port 1 of said splitter to a mixer and sends a signal from a port 2 of said splitter directly to a transmitting antenna further comprising a microwave source operatively connected to an isolator, an isolator operatively connected to said power splitter wherein said isolator prevents a reflected signal from reaching said microwave source, said power splitter operatively connected to said transmitting antenna and to said mixer, a receiver operatively connected to an analog-to-digital converter which is operatively connected to a data acquisition and computing unit, a sample holder placed between said transmitting antenna and said receiver, a temperature measurement device operatively connected to said sample holder and said data acquisition and computing unit, and a sensor display operatively connected to said data acquisition and computing unit.

2. The system of claim 1 wherein said circuit further includes an algorithm for phase correction at a single frequency, based on a linear relationship between attenuation per unit thickness and a dielectric constant wherein said algorithm is used to resolve phase ambiguity for samples with a thickness greater than the wavelength in said sample.

3. The system of claim 1 wherein said attenuation and phase shift measurements are used to determine a dielectric constant and dielectric loss factor of a said granular, powdered, or particulate matter.

* * * * *